United States Patent [19]

Sestanj et al.

[11] 4,391,816

[45] Jul. 5, 1983

[54] N-(NAPHTHALENYLTHIOXOMETHYL-)AMINOACID DERIVATIVES

[75] Inventors: Kazimir Sestanj, St. Laurent; Nedumparambil A. Abraham, Dollard des Ormeaux; Francesco Bellini, Mount Royal; Adi Treasurywala, Point Claire, all of Canada

[73] Assignee: Ayerst, McKenna & Harrison Inc., Montreal, Canada

[21] Appl. No.: 321,304

[22] Filed: Nov. 13, 1981

[30] Foreign Application Priority Data

Nov. 2, 1981 [CA] Canada .................................. 372054

[51] Int. Cl.³ .................. C07C 153/063; A61K 31/65; A61K 31/40
[52] U.S. Cl. .................................... 424/274; 424/319; 548/539; 560/10; 562/427
[58] Field of Search ............................ 560/13, 16, 10; 562/427; 424/319, 274; 260/326.33; 548/539

[56] References Cited

U.S. PATENT DOCUMENTS 3,489,793  1/1970  Bertelli ................................ 562/450
3,821,383  6/1974  Sestanj et al. ....................... 424/258

OTHER PUBLICATIONS

Allinger, "Organic Chemistry," pp. 532–537 (1971).
D. Dvornik et al., Science, 182, 1146(1973).
M. J. Peterson et al., Metabolism, 28 (Suppl. 1), 456(1979).
A. Lawson and C. E. Searle, J. Chem. Soc., 1556 (1957).
V. I. Cohen et al., Chem. Abstr., 86, 189582f (1977).
J. Voss and W. Walter, Chem. Abstr., 70, 11306a (1969).
Chem. Abstr., 61, 4333f (1964) for E. Cioranescu et al., Rev. Chim. Acad. Rep. Populaire Roumaine, 7 (2), 755 (1962).

Primary Examiner—Michael L. Shippen
Attorney, Agent, or Firm—Arthur E. Wilfond

[57] ABSTRACT

Herein disclosed are N-(naphthalenylthioxomethyl-)aminoacid derivatives having aldose reductase inhibiting activity. The derivatives are useful for treating diabetic complications.

19 Claims, No Drawings

N-(NAPHTHALENYLTHIOXOMETHYL)AMINOACID DERIVATIVES

RELATED APPLICATIONS

Related hereto are U.S. Patent Application Ser. No. 321,306, U.S. Patent Application Ser. No. 321,303 and U.S. Patent Application Ser. No. 321,300, all filed on the same date as this application.

This application relates to N-(naphthalenylthioxomethyl)aminoacid derivatives, therapeutically acceptable salts thereof, a process for their preparation, and to pharmaceutical compositions thereof. The derivatives have pharmacologic properties which render them beneficial for the treatment of diabetes mellitus and associated conditions.

For many years dibetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy and cataracts. These complications have been linked to the undesirable accumulation of sorbitol in diabetic tissue, which in turn result from the high levels of glucose characteristic of the diabetic patient.

In mammals, including humans, the key enzyme involved in the conversion of hexoses to polyols (the sorbitol pathway) is aldose reductase. J. H. Kinoshita and collaborators, see J. H. Kinoshita, et al., Biochem. Biophys. Acta., 158, 472 (1968) and references cited therein, have demonstrated that aldose reductase plays a central role in the etiology of galactosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesirable accumulation of sorbitol has been demonstrated in the lens, peripheral nervous cord and kidney of diabetic animals, see A. Pirie and R. van Heyningen, Exp. Eye Res., 3, 124 (1964); L. T. Chylack and J. H. Kinoshita, Invest. Ophthal., 8, 401 (1969) and J. D. Ward and R. W. R. Baker, Diabetol., 6, 531 (1970).

1,3-Dioxo-1H-benz[de]isoquinoline-2(3H)-acetic acid has been reported to be an effective inhibitor of aldose reductase, see D. Dvornik et al., Science, 182,1146 (1973), and to be useful for the treatment of diabetic complications such as diabetic cataracts, neuropathy, nephropathy and retinopathy, see K. Sestanj, N. Simard-Duquesne and D. M. Dvornik, U.S. Pat. No. 3,821,383, June 28, 1974. Other compounds having a similar utility are the thioxo-1H-benz-[de]isoquinoline-2(3H)-acetic acid derivatives and the 1H-benz-[de]isoquinoline-2(3H)-acetic acid derivative of K. Sestanj U.S. Patent Applications Ser. No. 92,397 and 92,604 respectively, both filed Nov. 8, 1979, now respectively U.S. Pat. Nos. 4,254,108 and 4,254,109. (S)-6-Fluoro-2,3-dihydrospiro(4H-1-benzopyran-4,4'-imidazolidine)-2',5'-dione (sorbinil) is still another compound that has received attention because of its aldose reductase inhibiting properties (see M. J. Peterson et al., Metabolism, 28 (Suppl. 1), 456 (1979). Accordingly, these compounds represent an important new approach for the treatment of diabetes mellitus.

The present application discloses novel N-(naphthalenylthioxomethyl)aminoacid derivatives which are effective inhibitors of aldose reductase. These new derivatives are structurally quite different from the above noted aldose reductase inhibitors. Close prior art compounds, on a structural basis, appear to be a group of thioacylaminoacids, e.g. N-phenylthioxomethyl-N-methylglycine, prepared by A. Lawson and C. E. Searle, J. Chem. Soc., 1556 (1957) as part of a chemical investigation of the chemical properties of such compounds. The last mentioned compounds were prepared by thiobenzoylation of various amino acids with (thiobenzoylthio)acetic acid. An important structural difference between these compounds and the present derivatives is the different type of aromatic group substituted on the thione portion of the thioamide. Thioacylamides also have been reported [see Chem. Abstr., 86, 189582f (1977) for V. I. Cohen et al., Eur. J. Med. Chem., 5, 480 (1976) and Chem. Abstr., 70, 11306a (1969) for von J. Voss and W. Walter, Justus Leibigs Ann. Chem., 716, 209 (1968)]. The structures of the thioacylamides of Cohen et al and Voss et al differ from the structure of the present derivatives by having at least a different type of N-substitution. Another close prior art compound, on a structural basis, is N-[(1-naphthalenyl)carbonyl]glycine, [see Chem. Abstr., 61, 4333f (1964) for E. Cioranescu et al., Rev. Chim. Acad. Rep. Populaire Roumaine, 7 (2) 755, (1962)]. The latter compound, which has been used as a chemical intermediate, is distinguished from the compounds of the present invention by being an amide and not a thioamide.

SUMMARY OF THE INVENTION

The N-(naphthalenylthioxomethyl)aminoacid derivatives of this invention are represented by formula I

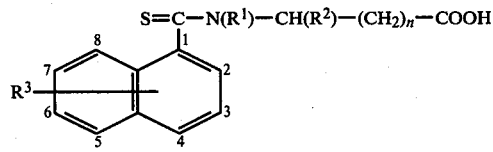

wherein $R^1$ is lower alkyl, carboxymethyl, phenyl or phenyl substituted with a substituent selected from halo, lower alkyl or lower alkoxy;

$R^2$ is hydrogen or lower alkyl;

n is the integer 0, 1 or 2; or n is the integer O and $R^1$ and $R^2$ form a $(CH_2)_3$ bridge to complete a pyrrolidine ring with the nitrogen and carbon to which $R^1$ and $R^2$ are joined; and $R^3$ is a halo substituent at position 3, 5, 6 or 7 of the naphthalene ring, or $R^3$ is two or three substituents on the naphthalene ring selected from the group consisting of 4-loower alkoxy-5-[di(lower alkyl)aminosulfonyl] and 3-halo-4-lower alkoxy-5-[di(lower alkyl)aminosulfonyl];

with the proviso that when $R^1$ is lower alkyl; then $R^3$ is a halo substituent at position 3, 6 or 7 of the naphthalene ring or $R^3$ is two or three substituents as defined herein; or a therapeutically acceptable salt thereof with an organic or inorganic base.

A group of preferred compounds is represented by compounds of formula I wherein $R^1$ is lower alkyl, carboxymethyl or phenyl substituted with a halo, $R^2$ is hydrogen or lower alkyl, n is O or 2, or n is O and $R^1$ and $R^2$ form a $(CH_2)_3$ bridge to complete a pyrrolidine ring with the nitrogen and carbon to which $R^1$ and $R^2$ are joined; and $R^3$ is as defined hereinbefore; or a therapeutically acceptable salt thereof with an organic or inorganic base.

Another preferred group of compounds is represented by compounds of formula I wherein $R^1$ is methyl, carboxymethyl or 4-chlorophenyl, $R^2$ is hydrogen or methyl, n is 0 or 2, or n is 0 and $R^1$ and $R^2$ form a pyrrolidine ring with the nitrogen and carbon to which $R^1$ and $R^2$ are joined; and $R^3$ is a bromo substituent at position 3, 5, 6 or 7 of the naphthalene ring, or $R^3$ is two or three substituents on the naphthalene ring selected from the group of 4-methoxy -5-(dimethylaminosulfonyl) and 3-chloro-4-methoxy-5-(dimethylaminosulfonyl), or a therapeutically acceptable salt thereof with an organic or inorganic base.

The compounds of formula I can be prepared by a process comprising the hydrolysis of an appropriate, corresponding ester of the compound of formula I. In a preferred embodiment, the ester has the formula

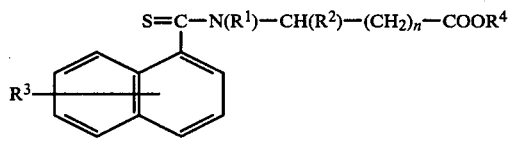

wherein $R^4$ is lower alkyl or ar(lower)alkyl and $R^1$, $R^2$, $R^3$ and n are as defined herein.

A method is provided for preventing or relieving diabetes mellitus associated complications in a diabetic mammal by administering to said mammal an prophylactic or alleviating amount of the compound of formula I or a therapeutically acceptable salt thereof with an organic or inorganic base.

The compound of formula I, or a therapeutically acceptable salt thereof with an organic or inorganic base, when admixed with a pharmaceutically acceptable carrier, forms a pharmaceutical composition which can be used according to the preceding method.

DETAILED DESCRIPTION OF THE INVENTION

The term "lower alkyl" as used herein means a straight chain alkyl radical containing from one to four carbon atoms or a branched chain alkyl radical containing three or four carbon atoms and includes methyl, ethyl, propyl, 1-methylethyl, butyl, 2-methylpropyl and 1,1-dimethylethyl. Preferred lower alkyl radicals contain one to three carbon atoms.

The term "lower alkenyl" as used herein means a straight chain alkenyl radical containing from two to six carbon atoms or a branched chain alkenyl radical containing from four to six carbon atoms and includes, for example, ethenyl, 2-propenyl, 2-methyl-2-propenyl and 2-ethyl-3-butenyl. Preferred lower alkenyl radicals contain two to three carbon atoms.

The term "lower alkoxy" as used herein means a straight chain alkoxy radical containing from one to six carbon atoms, preferably one to three carbon atoms, or a branched chain alkoxy radical containing three or four carbon atoms, and includes methoxy, ethoxy, 1-methylethoxy, butoxy and hexanoxy.

The term "halo" as used herein means halogens and includes fluoro, chloro, bromo and iodo.

The term "ar" as used mean an aromatic radical containing at least one benzene ring. The preferred aromatic radical is phenyl.

The compounds of formula I form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylenediamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

The compounds of this invention and their addition salts with pharmaceutically acceptable organic or inorganic bases may be administered to mammals, for example, man, cattle or rabbits, either alone or in dosage forms, i.e., capsules or tablets, combined with pharmacologically acceptable excipients, see below. Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2–7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the present therapeutic agents will vary with the form of administration and the particular compound chosen. Furthermore, it will vary with the particular host under treatment. Generally, treatment is initiated with small dosages substantially less than the optimal dose of the compound. Thereafter, the dosage is increased by small increments until efficacy is obtained. In general, the compounds of this invention are most desirably administered at a concentration level that will generally afford effective results without causing any harmful or deleterious side effects. For topical administration a 0.05–0.2% solution may be administered dropwise to the eye. The frequency of instillation varies with the subject under treatment from a drop every two or three days to once daily. For oral or parenteral administration a preferred level of dosage ranges from about 2 mg to about 200 mg per kilo of body weight per day, although aforementioned variations will occur. However, a dosage level that is in the range of from about 10 mg to about 50 mg per kilo of body weight per day is most satisfactory.

Unit dosage forms such as capsules, tablets, pills and the like may contain from about 25 to about 250 mg of the active ingredients of this invention, dependent on the type of unit dosage, preferably with a significant quantity of a pharmaceutical carrier. Thus, for oral administration, capsules can contain from between about 25 to about 250 mg of the active ingredients of this invention with or without a pharmaceutical diluent. Tablets, either effervescent or noneffervescent, can contain between about 25 to 250 mg the active ingredients of this invention together with conventional pharmaceutical carriers. Thus, tablets which may be coated and either effervescent or noneffervescent may be prepared according to the known art. Inert diluents or carriers, for example, magnesium carbonate or lactose, can be used together with conventional disintegrating agents for example, magnesium stearate.

Syrups or elixirs suitable for oral administration can be prepared from water soluble salts, for example, sodium N-[(5-bromo-1-naphthalenyl)thioxomethyl]-N-(4-chlorophenyl)glycinate, and may advantageously contain glycerol and ethyl alcohol as solvents or preservatives.

The compound of formula I, or a therapeutically acceptable salt thereof, also can be used in combination with insulin or oral hypoglycemic agents to produce beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compound of formula I, or a therapeutically acceptable salt thereof, can be administered sequentially or simultaneously with insulin or the oral hypoglycermic agent. Suitable methods of administration, compositions and doses of the insulin preparation or oral hypoglycemic agent are described in medical textbooks; for instance, "Physicians' Desk Reference", 34 ed., Medical Economics Co., Oradell, N.J., United States, 1980. When used in combination, the compound of formula I, or its therapeutically acceptable salt, is administered as described previously. The compound of formula I, or its therapeutically acceptable salt, can be administered with the oral hypoglycemic agent in the form of a pharmaceutical composition comprising effective amounts of each agent.

The aldose reductase inhibiting effects of the compounds of formula I and their pharmaceutically acceptable salts with organic or inorganic bases can be demonstrated by employing an in vitro testing procedure similar to that described by S. Hayman and J. H. Kinoshita, J. Biol. Chem., 240,877 (1965). In the present case the procedure of Hayman and Kinoshita is modified in that the final chromatography step is omitted in the preparation of the enzyme from bovine lens.

The following results were obtained when the compounds of this invention were evaluated in the above in vitro test.

| Compound of Formula I | | | | % Inhibition at Different Molar Concentrations (in vitro) | | |
| --- | --- | --- | --- | --- | --- | --- |
| $R^1$ | $R^2$ | $R^3$ | n | $10^{-5}$ | $10^{-6}$ | $10^{-7}$ |
| $CH_3$ | H | 3-Br | 0 | 90 | 74 | 28 |
| $CH_3$ | H | 6-Br | 0 | 91 | 75 | 18 |
| $CH_3$ | H | 7-Br | 0 | 86 | 58 | 15 |
| $CH_3$ | H | 4-$CH_3O$, 5-[$(CH_3)_2NSO_2$] | 0 | 80 | 35 | 6 |
| $CH_3$ | H | 3-Cl,4-$CH_3O$, 5-[$(CH_3)_2NSO_2$] | 0 | 91 | 67 | 19 |
| 4-Cl—$C_6H_4$ | H | 5-Br | 0 | 86 | 80 | 39 |
| $CH_3$ | H | 5-Br | 2 | 37 | — | — |
| $CH_3$ | $CH_3$ | 5-Br | 0 | 18 | — | —* |
| $CH_3$ | $CH_3$ | 5-Br | 0 | 32 | — | —** |
| $CH_2CH_2CH_2$ | | 5-Br | 0 | 56 | 26 | — |
| $CH_2COOH$ | H | 5-Br | 0 | 46 | 7 | — |

PROCESS

The compounds of this invention can be prepared by a process which is illustrated by the following reaction scheme in which $R^1$, $R^2$, $R^3$ and n are as defined hereinbefore and $COOR^4$ is an ester group which, for example, may be a lower alkyl or an ar(lower)alkyl [i.e. $R^4$ is lower alkyl or ar(lower)alkyl].

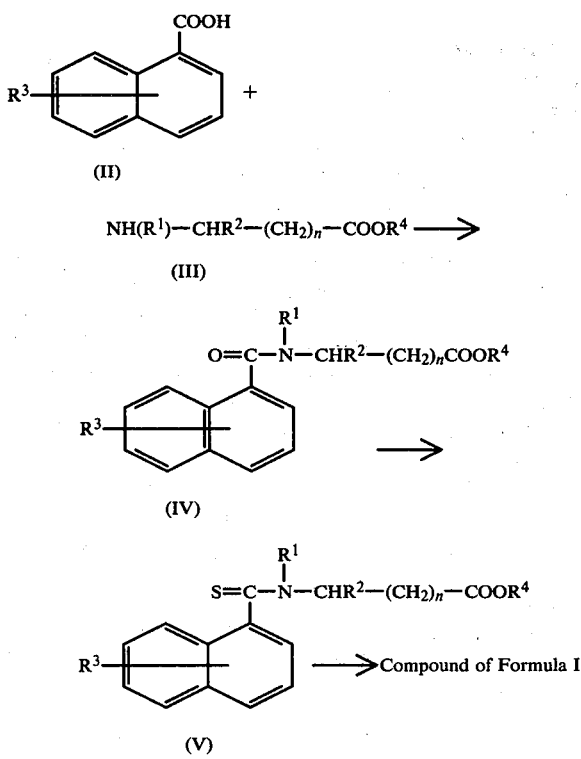

The starting materials of formula II are known or can be prepared by known methods. For example, see "Elsevier's Encyclopaedia of Organic Chemistry", F. Radt, Ed., Series III, vol 12B, Elsevier Publishing Co., Amsterdam, 1953, pp 3963-4473. A number of methods for preparing the starting materials is illustrated by examples 1, 1a and 1b, described hereinafter.

With reference to the reaction scheme, the starting material of formula II is coupled with the aminoacid ester of formula III to obtain the amidoester of formula IV by the "carboxyl activation" coupling procedure. Descriptions of carboxyl-activating groups are found in general textbooks of peptide chemistry; for example K. D. Kopple, "Peptides and Amino Acids", W. A. Benjamin, Inc., New York, 1966, pp. 45-51, and E. Schröder and K. Lübke, "The peptides"; Vol. 1, Academic Press, New York, 1965, pp.77-128. Examples of the activated form of the terminal carboxyl are the acid chloride, acid bromide, anhydride, azide, activated ester, or O-acyl urea of a dialkylcarbodiimide. Preferred activated forms of the carboxyl are the acid chloride or the 1-benzotriazolyl, 2,4,5-trichlorophenyl or succinimido activated esters.

Thereafter, the amido ester of formula IV is reacted under anhydrous conditions with about two to five molar equivalents of phosphorus pentasulfide in an inert solvent, e.g. xylene or toluene, to obtain the corresponding thioxoester of formula V. This reaction is performed conveniently at temperatures ranging from 80° to about 150° C. and at times ranging from 20 minutes to four hours. Preferably, this reaction is performed in the presence of an organic base for instance, N-ethyl morpholine, triethylamine or pyridine.

Finally, the thioxoester of formula V is hydrolyzed with a hydrolyzing agent to give the corresponding product of formula I. Generally speaking, this conversion is most conveniently performed by employing a base as the hydrolyzing agent. The hydrolysis is performed in the presence of sufficient water, followed by acidification of the reaction mixture to yield the desired acid. However, it should be understood that the manner of hydrolysis for the process of this invention is not intended to be limited to basic hydrolysis, since hydrolysis under acidic conditions and other variations, for example, treatment with lithium iodide in collidine (see L. F. Fieser and M. Fieser, "Reagents for Organic Synthesis", John Wiley and Sons, Inc., New York, 1969, pp. 615-617), are also applicable. For the hydrolysis of tert butyl esters, acidic hydrolysis is preferred.

For basic hydrolysis, a peferred embodiment involves subjecting the ester to the action of a strong base, for example, sodium or potassium hydroxide, in the presence of sufficient water to effect hydrolysis of the ester. The hydrolysis is performed using a suitable solvent, for example, methanol, ethanol or 2-methoxyethanol. The reaction mixture is maintained at a temperature of from about 25° to 100° C. or at the reflux temperature of the solvent employed until hydrolysis occurs. Usually from 10 minutes to 6 hours is sufficient for this hydrolysis. The reaction mixture is then rendered acidic with an acid, for example, acetic acid, hydrochloric acid or sulfuric acid to release the free acid.

It will be appreciated by those skilled in the art that when it is desired to prepare compounds of formula I in which $R^1$ is carboxymethyl, then the corresponding group for the intermediates of formulae III, IV and V should be protected to avoid any possible intereference with the coupling step and subsequent reaction with phosphorus pentasulfide. For convenience, the protective group should be one which is capable of being removed during the subsequent hydrolysis of compound V without affecting the end product, namely the compound of formula I. A suitable protective group is the lower alkyl or ar(lower)alkyl ( i.e. the carboxyl group is protected in the form of its lower alkyl ester or its ar(lower)alkyl ester). Preferably, and for practical reasons, the protective group is the same lower alkyl or ar(lower)alkyl radical as the radical $R^4$ of the intermediates. In otherwords, the desired compound of formula I is obtained provided that the carboxyl group of the carboxymethyl in the corresponding intermediates of formula III, IV and V is protected with a protective group capable of being removed under hydrolysis conditions not affecting the compound of formula I.

Finally, it is noted that the compounds of this invention, represented by formula I, can exist in rotameric forms. More explicitly, mesomerism imparts a partial double bond character to the carbon-nitrogen bond of the thioamide group. This partial double bond character leads to restricted rotation about the carbon nitrogen bond giving rise to cis and trans rotamers, the restricted rotation being augmented by the bulkiness of neighboring groups. interconversion of the rotamers is possible and is dependent on the physical environment. As evidenced by its physical properties, the thermodynamically more stable rotamer exists exclusively in the crysalline state of the compound and is the predominant isomer present in equilabrated solutions. Furthermore, the more stable rotamer is the more pharmacologically active. The less stable rotamer can be separated from the more stable rotamer by high performance liquid chromatography or by thin layer chromatography. The rotameric forms are included within the scope of this invention. For brevity, the compounds of this invention, including their rotameric forms, are referred to herein as compounds of formula I.

The following examples illustrate further this invention.

EXAMPLE 1

7-Bromo-1-naphthalenecarboxylic Acid (II, $R^3=$7-Br)

A sodium hypochlorite solution was prepared by introducing chlorine gas (28 g, 0.79 mole) into a solution of NaOH (38 g) in 600 ml of ice water. Solid (7-bromo-1-naphthalenyl)ethanone (19.7 g, 0.079 mole) was added to the stirred sodium hypochlorite solution at 0° C. and then the mixture was heated on a steam bath for 1 hr. The precipitate was removed by filtration. Sodium metabisulfite (10 g) was added to the cooled (0° C.) filtrate. The mixture was adjusted to pH 5 with concentrated HCl. The precipitate was collected and dried. The collected precipitate was crystallized from boiling ethanol by the addition of water to afford 14.7 g (two crops) of the title compound; mp 227–230° C.; NMR ($CDCl_3$) δ 7.55–8.35 (m, 5H), 9.11 (d, J=2 Hz, 1H); IR ($CHCl_3$) 2800, 1672, 1609, 1683, 1668 $cm^{-1}$.

EXAMPLE 1a

4-Methoxy-5-(dimethylaminosulfonyl)-1-naphthalenecarboxylic Acid [II, $R^3=$4-$CH_3O$ and 5-$(CH_3)_2NSO_2$]

Dry dimethylamine gas was passed through a solution of 1,8-naphthasultone [5.0 g, 24 mmoles, described by I. Hideo, Japanese Patent 4927, Aug. 31, 1951; Chem. Abstr., 47, 9364b (1953)] for 1.5 hr at 20°–22° C. The mixture was stirred for 20 hr. The resulting yellow crystals were collected by filtration. The filtrate was concentrated to give more crystals. The two batches of crystals were combined giving 5 g of 8-hydroxy-N,N-dimethyl-1-naphthalenesulfonamide; mp 95° C.; NMR ($CDCl_3$) δ 2.88 (s, 6H), 7.1–8.3 (m, 6H).

The latter compound (2.74 g, 11 mmoles) was dissolved in 2 N aqueous NaOH (5.9 ml). Dimethyl sulfate (2.06 ml, 11 mmoles) was added dropwise to the stirred solution kept at 40° to 45° C. by a water bath, the solution being kept at pH 7.5 by the simultaneous addition (dropwise) of 2 N aqueous NaOH. Thereafter, the mixture was stirred for 30 min at 50° C. The precipitate was collected and recrystallized from ethyl acetate to give 2.1 g of 8-methoxy-N,N-dimethyl-1-naphthalenesulfonamide, mp 146°–149° C.

The latter compound (2.1 g, 7.9 mmoles) was mixed with acetyl chloride (9 ml) and nitrobenzene (158 ml). The mixture was added portionwise to stirred anhydrous aluminum chloride. The resulting mixture was stirred at 60°–70° C. for 1 hr and then at 100° C. for 4.5 hr. The mixture was poured into a second mixture of ice water (1 liter) and concentrated HCl (180 ml). The resulting mixture was stirred for 30 min and then the lower nitrobenzene layer was separated. The upper aqueous layer was extracted (2×) with chloroform. The organic layers were combined, washed with brine, dried ($Na_2SO_4$) and evaporated to dryness. The residue was dissolved in ethyl acetate-hexane (1:1) and passed through a column of silica gel (300 g). The appropriate fractions were pooled and concentrated to dryness. The residue was crystallized from ethyl acetate-hexane (1:1) to give 8.9 g of 5-acetyl-8-methoxy-N,N-dimethyl-1-naphthalenesulfonamide, mp 124°–127° C.

The latter compound (8.25 g, 27 mmoles) was added at 20°–22° C. to a solution of sodium hypochlorite which was prepared immediately before use by bubbling chlorine (8.6 g, 12 mmoles) into an ice cold mixture of NaOH (11.6 g, 29 mmoles), water (159 ml) and ice (66 g). The reaction mixture was warmed to 55° C. An exothermic reaction took place. Thereafter, the mixture was stirred at 60°–70° C. for 5 hr during which time the reaction mixture became a clear solution and then formed a precipitate. The mixture was stirred for 18 additional hours at 20°–22° C. Insoluble material in the reaction mixture was separated by filtration. The filtrate was washed with ethyl acetate, and upon careful addition of sodium bisulfite (2.6 g in 10 ml of water) to the filtrate, a precipitate was obtained. The latter precipitate was collected, washed with water and dried over $P_2O_5$ to give 7.6 g of the title compound; mp 220°–221° C.; NMR ($CDCl_3$) δ 3.07 (s, 6H), 4.1 (s, 3H), 8.0 (m, 5H), 10.0 (broad, 1H).

EXAMPLE 1b

3-Chloro-4-methoxy-5-(dimethylaminosulfonyl)-1-naphthalenecarboxylic Acid [II, $R^3=$3-Cl, 4-$CH_3O$ and 5-$(CH_3)_2NSO_2$]

4-Methoxy-5-(dimethylaminosulfonyl)-1-naphthalenecarboxylic acid (15.26 g, 50 mmoles), described in Example 1a) was suspended in acetic acid (46 ml). Sulfuryl chloride (6 ml, 75 mmoles) was added portionwise to the suspension at such a rate that the temperature did not exceed 32° C. The resulting solution was stirred at 20°–22° C. for 2 hr and then poured into 460 ml of ice water. The mixture was stirred for 30 min. The precipitate was collected and dried over $P_2O_5$ to give 16.7 g of the title compound; mp 127°–137° C.; NMR ($CDCl_3$) δ 3.05 (s, 6H), 4.12 (s, 3H), 8.0 (broad, 1H), 7.7 and 9.25 (m, 4H).

EXAMPLE 2

N-[(3-Bromo-1-naphthalenyl)carbonyl]-N-methylglycine Methyl Ester (IV, $R^1=CH_3$, $R^2=$H, $R^3=$3-Br, n=O and $R^4=CH_3$)

Procedure A

A solution of the starting material of formula II, 3-bromo-1-naphthalenecarboxylic acid [12.0 g, 47.8 mmoles, described by H. G. Rule and S. B. Thompson, J. Chem. Soc., 1764 (1937)], in thionyl chloride (120 ml) was refluxed for 5 min and then cooled in an ice bath. Dimethylformamide (DMF, 5 drops) was added to the mixture. The mixture was refluxed for 15 min. The resulting solution was evaporated to dryness under reduced pressure. The residue was dissolved in benzene and the solution was taken to dryness under reduced pressure. The residue (11.4 g) was suspended in pyridine (100 ml). N-Methylglycine hydrochloride (5.6 g, 40.3 mmoles) in triethylamine (5.6 ml, 40.3 mmoles), a starting material of formula III, was added to the suspension. The resulting mixture was stirred at 20°–22° C. for 20 min and then poured into water (500 ml). The aqueous mixture was extracted with chloroform. The extract was washed with 2 N aqueous HCl, a saturated solution of $NaHCO_3$ and water, dried ($MgSO_4$) and evaporated to dryness. The residue (13 g) was subjected to chromatography on silica gel (300 g) using acetone-toluene (1:4) as eluant. Evaporation of the pooled fractions gave 10 g of the title compound as an oil; NMR ($CDCl_3$) δ 2.80 and 3.20 (2s, 3H), 3.6 and 3.8 (2s, 3H), 4.35 (m, 2H), 7.1–8.0 (m, 6H); IR($CHCl_3$) 1730, 1620 $cm^{-1}$.

Procedure B

A mixture of the starting material of formula II, 3-bromo-1-naphthalenecarboxylic acid (12.8 g, 52 mmoles), and 1-hydroxybenzotriazole (HOBt, 7.0 g, 52 mmoles) in DMF (200 ml) was prepared. N,N,-dichlohexylcarbodiimide (DCC, 10.6 g, 52 mmoles) in DMF (30 ml) was added to the mixture. The resulting mixture was stirred at 20° C. for 1 hr and then cooled again to 0° C. N-Methylglycine methyl ester hydrochloride (7.25 g, 52 mmoles) and then N-ethylmorpholine (6.7 ml, 52 mmoles) were added to the cooled mixture. The mixture was stirred for 30 min at 0° C. and then for 18 hr at 20° C. Thereafter, the mixture was filtered and concentrated to dryness under reduced pressure. The residue was subjected to chromatography on 325 g of silica gel using ethyl acetate-hexane (1:1) as the eluant. The pure fractions were pooled to yield 10.5 g of product which was recrystallized from ethyl acetate to give the title compound, identical to the product of procedure A of this example.

EXAMPLE 3

N-[(3-Bromo-1-napthalenyl)thioxomethyl]-N-methylglycine Methyl Ester (V, $R^1=CH_3$, $R^2=H$, $R^3=3$-Br, n=O and $R^4=CH_3$)

To a stirred solution of N-[(3-bromo-1-naphthalenyl)-carbonyl]-N-methylglycine methyl ester (6.0 g, 17 mmoles, described in Example 2) in dry pyridine (60 ml), phosphorus pentasulfide (6.8 g, 31 mmoles) was added portionwise. The mixture was stirred and refluxed for 2 hr and then poured into 600 ml of warm water (caution: evolution of copious quantities of $H_2S$). The mixture was cooled to 20° to 22° C. (room temperature) and then extracted with chloroform. The extract was washed with 2 M aqueous HCl solution and water, dried (MgSO$_4$), filtered and evaporated to dryness. The residue was purified by chromatography on silica gel (300 g) using acetone-toluene (1:4) as eluant. Pooling of the fractions gave 4.7 g of the title compound; mp 128°-130° C.; NMR (CDCl$_3$) δ 3.0 (s, 3H), 3.82 (s, 3H), 4.50 and 5.30 (d, J=16.5 Hz, 2H), 7.2–7.9 (m, 6H); IR (CHCl$_3$) 1730 cm$^{-1}$.

By following serially the procedures of Examples 2 and 3 and using the appropriate starting material of formula II instead of 5-bromo-1-naphthalenecarboxylic acid, other compounds of formula V in which $R^1$ and $R^4$ each is methyl, $R^2$ is hydrogen and n is zero are obtained. Examples of the latter compounds are listed as products in Table I together with the appropriate starting material of formula II used for their preparation.

TABLE I

| EXAMPLE | STARTING MATERIAL OF FORMULA II $R^3$ | PRODUCT: |
|---|---|---|
| 4 | 6-Br | N—[(6-bromo-1-naphthalenyl)-thioxomethyl]-N—methylglycine methyl ester; NMR (CDCl$_3$) δ 3.0 (s, 3H), 3.85 (s, 3H), 4.50 & 5.35 (d, J = 16.5 Hz, 2H), 7.1–8.0 (6H); IR (CHCl$_3$) 1735 cm$^{-1}$ |
| 5 | 7-Br | N—[7-bromo-1-naphthalenyl)-thioxomethyl]-N—methylglycine methyl ester; NMR (CDCl$_3$) δ 3.03 (s, 3H), 3.90 (s, 3H), 4.53 & 5.35 (2d, J = 17Hz, 2H), 7.25–7.85 (m, 5H), 8.15 (d, 1H); IR (CHCl$_3$) 1740, 1606, 1580 cm$^{-1}$; UVλmax(EtOH) 328 nm (ε 1760), 280 (13,260), 222 (53,540) |
| 6 | 4-CH$_3$O, 5-(CH$_3$)$_2$NSO$_2$ | N—[[4 methoxy-5-(dimethylaminosulfonyl)-1-naphthalenyl]-thioxomethyl]-N—methylglycine methyl ester; mp 127–130° C.; NMR (CDCl$_3$) δ 3.0 (s, 3H), 3.07 (s, 6H), 3.85 (s, 3H), 4.05 (s, 3H), 4.47 & 5.45 (d, J = 16.5, 2H), 7.5 (m, 5H) |
| 7 | 3-Cl,4-CH$_3$O, 5-(CH$_3$)$_2$NSO$_2$ | N—[[3-chloro-4-methoxy-5-(dimethylaminosulfonyl)-1-naphthalenyl]thioxomethyl]-N—methylglycine methyl ester; mp 190° C.; NMR (CDCl$_3$) δ 3.05 (s, 9H), 3.8 (s, 3H), 4.05 (s, 3H), 4.45 & 5.4 (2d, J = 20 Hz, 2H) |

With reference to Table I, the starting material of formula II are described by M. J. S. Dewar and P. J. Grisdale, J. Am. Chem. Soc., 84, 3541 (1962) for example 4; in example 1 for example 5; in example 1a for example 6; and in example 1b for example 7.

By following serially the procedure of examples 2 and 3, but using 5-bromo-1-naphthalenecarboxylic acid as the starting material of formula II and the appropriate starting material of formula III instead of N-methylglycine, other compounds of formula V are obtained. Examples of such compounds are listed in Table II together with the appropriate starting material of formula III used for their preparation.

TABLE II

| EXAMPLE | STARTING MATERIAL OF FORMULA III | | | | PRODUCT: N—[(5-BROMO-1-NAPHTHALENYL)THIOXO-METHYL]-suffix listed below |
|---|---|---|---|---|---|
| | $R^1$ | $R^2$ | n | R | |
| 8 | 4-Cl—$C_6H_4$ | H | 0 | $C_2H_5$ | N—(4-chlorophenyl)glycine ethyl ester; mp 188–189° C.; NMR ($CDCl_3$) δ 1.35 (t, J = 7Hz, 3H), 4.3 (q, J = 7Hz, 2H), 4.7 & 5.35 (2d, J = 16.5 Hz, 2H), 7.5 (m, 10H); IR ($CHCl_3$) 1740 cm; UVλmax (EtOH) 286 nm (ε 17,030), 220 (46,190) |
| 9 | $CH_3$ | H | 2 | $CH_3$ | N—methyl-4-aminobutanoic acid methyl ester; NMR ($CDCl_3$) δ 1.5–2.6 (m, 2H), 2.9 & 3.5 (2s, 2H), 3.65 & 3.7 (2s, 2H), 4.2 (m, 2H), 7.2–8.3 (broad, 6H) |
| 10 | $CH_3$ | $CH_3$ (N—methyl-D-alanine methyl ester) | 0 | $CH_3$ | N—methyl-D-alanine methyl ester; NMR ($CDCl_3$) δ 1.65 (m, 3H), 2.85 (s, 3H), 3.5 & 3.7 (2d, 3H), 6.65 (q, 1H), 7.15–8.3 (m, 6H) |
| 11 | $CH_3$ | $CH_3$ (N—methyl-L-alanine methyl ester) | 0 | $CH_3$ | N—methyl-L-alanine methyl ester; NMR ($CDCl_3$) δ 1.5 (m, 3H), 2.85 (s, 3H), 3.55 & 3.85 (2d, 3H), 6.65 (q, 1H), 7.2–8.25 (m, 6H) |
| 12 | $CH_2CO—OCH_3$ | H | 0 | $CH_3$ | N—(carboxymethyl)glycine dimethyl ester; NMR ($CDCl_3$) δ 3.60 (s, 3H), 3.85 (s, 3H), 4.07 (s, 2H), 4.46 & 5.45 (d, 2H), 7.15–8.30 (m, 6H) |
| 13 | $CH_2CH_2CH_2$ | | 0 | $CH_3$ | L-proline methyl ester; mp 155–158° C.; NMR (DMSO—$d_6$) δ 1.9 (m, 2H), 3.2 (m, 2H), 5.05 (m, 1H), 3.7 & 3.75 (2s, 3H), 7.35–8.2 (m, 6H) |

With reference to Table II the starting materials of formula III are described by G. C. Finger et al., J. Med. Chem., 8, 405 (1965) for example 8; by S. M. McElvin and J. F. Vozza, J. Am. Chem. Soc., 71, 896 (1449) for example 9; by P. Quitt et al., Helv. Chim, Acta, 46, 327 (1963) concerning the corresponding free acids for examples 10 and 11; and by W. J. A. Jongkees, Recl. Trav. Chim., 27, 287 (1908) for example 12. L-Proline methyl ester of Example 13 is available commercially.

EXAMPLE 14

N-[(3-Bromo-1-naphthalenyl)thioxomethyl]-N-methylglycine (I, $R^1=CH_3$, $R^2=H$, $R^3=3$-Br and n=O)

N-[(3-Bromo-1-naphthalenyl)thioxomethyl]-N-methylglycine methyl ester (4.7 g, 13 mmoles, described in example 3) was suspended in methanol (42 ml). An 1 N aqueous NaOH solution (18 ml, 18 mmoles) was added to the suspension. The mixture was refluxed until a clear solution resulted (about 30 min). The solution was evaporated to dryness under reduced pressure. The residue was dissolved in water. The aqueous solution was extracted with chloroform, rendered acidic with 2 N aqueous HCl solution and extracted with ethyl acetate. The ethyl acetate extract was dried ($MgSO_4$) and evaporated to dryness. The residue was crystallized from diethyl ether-hexane to afford the title compound; mp 165°–167° C.; NMR (DMSO-$d_6$) δ 3.05 (s, 3H), 4.65 and 5.30 (d, J=16.5 Hz, 2H), 7.2–7.9 (m, 6H), 9.2 (broad, 1H); Anal Calcd: C, 49.72% H, 3.58% N, 4.14%; Found: C, 49.81% H, 3.64% N, 4.16%.

In the same manner, but replacing N-[(3-bromo-1-naphthalenyl)thioxomethyl]-N-methylglycine methyl ester with an equivalent amount of an ester of formula V, prepared in examples 4 to 13, the respective, corresponding compounds of formula I are obtained:

N-[(6-bromo-1-naphthalenyl)thioxomethyl)-N-methylglycine (I, $R^1=CH_3$, $R^2=H$, $R^3=6$-Br and n=O); mp 174°–175° C.; NMR (DMSO-$d_6$) δ 2.95 (s, 3H), 4.65 and 5.15 (d, J=17 Hz, 2H), 7.7 (m, 6H), 10.9 (broad, 1H); Anal Calcd: C, 49.72% H, 3.58% N, 4.14%; Found: C, 50.13% H, 3.68% N, 4.13%;

N-[(7-bromo-1-naphthalenyl)thioxomethyl]-N-methylglycine (I, $R^1=CH_3$, $R^2=H$, $R^3=7$-Br and n=O); mp 169°–171° C.; NMR ($CDCl_3$) δ 3.05 and 3.70 (2s, 3H), 4.07 (s, 1H), 4.67 and 5.40 (2d, J=17 Hz, 1H), 7.50 (m, 5H), 8.69 (s, 1H), 8.40 (broad, 1H); IR (Nujol *) 2800, 1715 $cm^{-1}$; UVλmax (EtOH) 280 nm (ε 14,170), 223 (58,040);

*Nujol is a trademark for a brand of white mineral oil.

Anal Calcd: C, 49.72% H, 3.58% N, 4.14%; Found: C, 50.02% H, 3.57% N, 4.21%; N-[[4-methoxy-5-(dimethylaminosulfonyl)-1-naphthalenyl]thioxomethyl]-N-methylglycine[I, $R^1=CH_3$, $R^2=H$, $R^3=4-CH_3O$ and 5-[$(CH_3)_2NSO_2$] and n=O]; mp 102°–104° C.; NMR ($CDCl_3$) δ 2.97 and 3.02 (2s, 6H), 3.45 (s, 3H), 4.03 (s, 3H), 4.55 and 5.35 (d, J=17.5 Hz, 2H), 6.2 (s, 1H), 7.6 (m, 5H); IR ($CHCl_3$) 3000, 1720 (with inflection at 1745), 1325, 1145 $cm^{-1}$; UVλmax (EtOH) 322 nm (ε 6,150), 254 (18,800);

Anal Calcd C, 51,49% H, 5.08% N, 7.06%, Found: C, 50.63% N, 5.58% N, 6.53%; N-[[3-chloro-4-methoxy-5-(dimethylaminosulfonyl)-1-naphthalenyl]thioxomethyl]-N-methylglycine [I, $R^1=CH_3$, $R^2=H$, $R^3=3$-Cl, 4-$CH_3O$, 5-[$(CH_3)_2NSO_2$] and n=O]; NMR ($CDCl_3$) δ 3.03 (s, 3H), 3.07 and 4.05 (2s, 3H), 4.58 and 5.36 (2d, J=17 Hz, 2H), 7.3–8.3 (m, 4H); IR ($CHCl_3$) 3000, 1725

(with inflection at 1755), 1340, 1150 cm$^{-1}$; UVλmax (EtOH) 316 nm (ε 6,080), 232 (43,310), 214 (39,690);

Anal Calcd: C, 47.38% H, 4.44% N, 6.50%; Found: C, 48.92% H, 5.05% N, 5.91%;

N-[(5-bromo-1-naphthalenyl)thioxomethyl]-N-(4-chlorophenyl)glycine (I, R$^1$=4-Cl-C$_6$H$_4$, R$^2$=H, R$^3$=5-Br and n=O); mp 90°-92° C.; NMR (CDCl$_3$) 67 4.92 and 5.37 (2d, J=17 Hz, 2d), 6.7-8.4 (m, 10H); IR (CHCl$_3$) 3000, 1720, 1584, 1562 cm$^{-1}$; UVλmax (EtOH) 287 nm (ε 16,521), 222 (38,910); Anal Calcd: C, 52,49% H, 3.01% N, 3.22%; Found: C, 52.52% H, 3.37% N, 307%;

N-[(5-bromo-1-naphthalenyl)thioxomethyl]-N-methyl-4-aminobutanoic acid (I, R$^1$=CH$_3$, R$^2$=H, R$^3$=5-Br and n=2); mp 167°-171° C.; NMR (DMSO-d$_6$) δ 2.00 (m, 2H), 2.88 and 3.57 (2s, 3H), 3.22 and 4.18 (2t, J=8 Hz and J=7 Hz, 2H), 7.4-8.4 (m, 6H); IR (Nujol *) 3000, 1703, 1580, 1558 cm$^{-1}$; UVλmax (EtOH) 273 nm (ε 15,856), 219 (42,369); Anal Calcd: C, 52.46% H, 4.44% N, 3.81%; Found: C, 52.06% H, 4.63% N, 3.81%;

*Trademark.

N-[(5-bromo-1-naphthalenyl)thioxomethyl]-N-methyl-D-alanine (I, R$^1$ and R$^2$=CH$_3$, R$^3$=5-Br and n=O); [α]$_D^{20}$+37.9° (c=1% in MeOH); NMR (CDCl$_3$) δ 1.67 and 1.70 (2d, J=7 Hz, 3H), 2.87 and 3.55 (2s, 3H), 4.45 (m, 1H), 7.0-8.4 (m, 6H);

IR (CHCl$_3$) 2900, 1720 cm$^{-1}$; UVλmax (EtOH) 278 nm (ε 13,520), 219 (40,080);

Anal Calcd: C, 51.14% H, 4.01% N, 3.98%; Found: C, 51.35% H, 4.42% N, 3.85%; N-[(5-bromo-1-naphthalenyl)thioxomethyl]-N-methyl-L-alanine (I, R$^1$ and R$^2$=CH$_3$, R$^3$=5-Br and N=O); [α]$_D^{20}$−37.6 (c=1% in MeOH); NMR (CDCl$_3$δ 1.67 and 1.70 (2d, J=7 Hz, 3H), 2.87 and 3.55 (2s, 3H), 4.45 (m, 1H), 7.0-8.4 (m, 6H);

IR (CHCl$_3$) 3000, 1717 cm$^{-1}$; UVλmax (EtOH) 278 nm (ε 13,710), 220 (40,920);

Anal Calcd: C, 51.14% H, 4.01% N, 3.98%; Found: C, 51.03% H, 4.37% N, 3.93%; N-[(5-bromo-1-naphthalenyl)thioxomethyl]-N-(carboxymethyl)glycine (I R$^1$=CH$_2$COOH, R$^2$=H, R$^3$=5-Br and n=O); mp 189°-191° C.; NMR (DMSO-d$_6$) δ 3.8 (d, J=18 Hz, 1H), 4.3 (d, J=18 Hz, 1H), 4.55 (d, J=18 Hz, 1H), 5.15 (d, J=18 Hz, 1H), 7.7 (m, 6H); IR (Nujol *) 2900, 1720 cm$^{-1}$; UVλmax (EtOH) 277 nm (13,945), 220 (41,180); Anal Calcd: C, 47.11% H, 3.17% N, 3.67%, Found: C, 46.91% H, 2.99% N, 3.56%; and

*Trademark.

N-[(5-bromo-1-naphthalenyl)thioxomethyl]-L-proline (I, R$^1$ and R$^2$ together=(CH$_2$)$_3$, R$^3$=5-Br and n=O); NMR (CDCl$_3$) δ 2.10 (m, 2H), 3.2 (t, J=7 Hz, 2H), 5.28 (m, 1H), 7.0-8.5 (m, 7H); IR (CHCl$_3$) 3000, 1710 cm$^{-1}$; UVλmax (EtOH) 282 nm (ε 14,500), 219 (42,000); Anal Calcd: C, 52.76% H, 3.87% N, 3.84%; Found: C, 52.44% H, 4.11% N, 3.79%.

We claim:

1. A compound of formula I

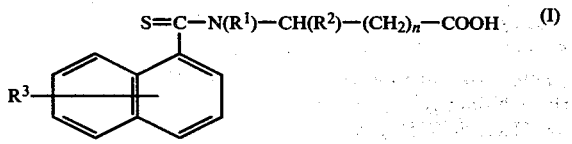

wherein

R$^1$ is lower alkyl, carboxymethyl, phenyl or phenyl substituted with a substituent selected from halo, lower alkyl or lowe alkoxy;

R$^2$ is hydrogen or lower alkyl;

n is the integer O, 1 or 2; or n is the integer O and R$^1$ and R$^2$ form a (CH$_2$)$_3$ bridge to complete a pyrrolidine ring with the nitrogen and carbon to which R$^1$ and R$^2$ are joined; and R$^3$ is a halo substituent at position 3, 5, 6 or 7 of the naphthalene ring, or R$^3$ is two or three substituents on the naphthalene ring selected from the group consisting of 4-lower alkoxy-5-[di(lower alkyl)aminosulfonyl] and 3-halo-4-lower alkoxy-5-[(di(lower alkyl)aminosulfonyl];

with the proviso that when R$^1$ is lower alkyl, then R$^3$ is a halo substituent at position 3, 6 or 7 of the naphthalene ring or R$^3$ is two or three substituents as defined herein, or a therapeutically acceptable salt thereof with an organic or inorganic base.

2. The compound of claim 1 wherein R$^1$ is lower alkyl, carboxymethyl or phenyl substituted with a halo, R$^2$ is hydrogen or lower alkyl, n is O or 2, or n is O and R$^1$ and R$^2$ form a (CH$_2$)$_3$ bridge to complete a pyrrolidine ring with the nitrogen and carbon to which R$^1$ and R$^2$ are joined; and R$^3$ is as defined in claim 1; or a therapeutically acceptable salt thereof with an organic or inorganic base.

3. The compound of claim 1 wherein R$^1$ is methyl, carboxymethyl or 4-chlorophenyl, R$^2$ is hydrogen or methyl, n is O or 2, or n is O and R$^1$ and R$^2$ form a pyrrolidine ring with the nitrogen and carbon to which R$^1$ and R$^2$ are joined; and R$^3$ is a bromo substitutent at position 3, 5, 6 or 7 of the naphthalene ring, or R$^3$ is two or three substituents on the naphthalene ring selected from the group of 4-methoxy-5-(dimethylaminosulfonyl) and 3-chloro-4-methoxy-5-(dimethylaminosulfonyl); or a therapeutically acceptable salt thereof with an organic or inorganic base.

4. N-[(3-Bromo-1-naphthalenyl)thioxomethyl]-N-methylglycine, as claimed in claim 1.

5. N-[(6-Bromo-1-naphthalenyl)thioxomethyl]-N-methylglycine, as claimed in claim 1.

6. N-[(7-Bromo-1-naphthalenyl)thioxomethyl]-N-methylglycine, as claimed in claim 1.

7. N-[[4-Methoxy-5-(dimethylaminosulfonyl)-1-naphthalenyl]thioxomethyl]-N-methylglycine, as claimed in claim 1.

8. N-[[3-Chloro-4-methoxy-5-(dimethylaminosulfonyl)-1-naphthalenyl]-thioxomethyl]-N-methylglycine, as claimed in claim 1.

9. N-[(5-Bromo-1-naphthalenyl)thioxomethyl]-N-(4-chlorophenyl)glycine, as claimed in claim 1.

10. N-[(5-Bromo-1-naphthalenyl)thioxomethyl]-N-methyl-4-aminobutanoic acid, as claimed in claim 1.

11. N-[(5-Bromo-1-naphthalenyl)thioxomethyl]-N-methyl-D-alanine, as claimed in claim 1.

12. N-[(5-Bromo-1-naphthalenyl)thioxomethyl]-N-methyl-L-alanine, as claimed in claim 1.

13. N-[(5-Bromo-1-naphthalenyl)thioxomethyl]-L-proline, as claimed in claim 1.

14. N-[(5-Bromo-1-naphthalenyl)thioxomethyl]-N-(carboxymethyl)glycine, as claimed in claim 1.

15. A pharmaceutical composition for preventing or relieving diabetic complications in a diabetic mammal which comprises a compound of claim 1, or a therapeutically acceptable salt thereof with an organic or inorganic base, and a pharmaceutically acceptable carrier.

16. The pharmaceutical composition of claim 15 which also comprises an oral hypoglycemic agent.

17. A method of preventing or relieving diabetic complications in a diabetic mammal which comprises administering to said mammal an alleviating or prophylactic amount of a compound of claim 1, or a therapeutically acceptable salt thereof with an organic or inorganic base.

18. The method of claim 17 in which the administration of the compound of claim 1 is performed simultaneously or sequentially with the administration of an effective blood glucose lowering amount of insulin or an oral hypoglycemic agent.

19. A compound of the formula

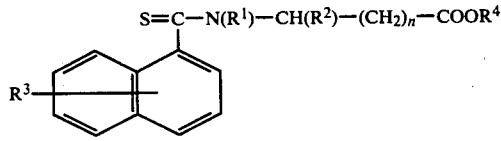

wherein
$R^1$ is lower alkyl, carboxymethyl, phenyl or phenyl substituted with a substituent selected from halo, lower alkyl or lower alkoxy;
$R^2$ is hydrogen or lower alkyl;
n is the integer O, 1 or 2; or
n is the integer O and $R^1$ and $R^2$ form a $(CH_2)_3$ bridge to complete a pyrrolidine ring with the nitrogen and carbon to which $R^1$ and $R^2$ are joined; and
$R^3$ is a halo substituent at position 3, 5, 6 or 7 of the naphthalene ring, or
$R^3$ is two or three substituents on the naphthalene ring selected form the group consisting of 4-lower alkoxy-5-[di(lower alkyl)aminosulfonyl] and 3-halo-4-lower alkoxy-5-[di(lower alkyl)aminosulfonyl];
with the proviso that when $R^1$ is lower alkyl, then $R^3$ is a halo substituent at position 3, 6 or 7 of the naphthalene ring or $R^3$ is two or three substituents as defined herein;
and $R^4$ is lower alkyl or ar(lower)alkyl.

* * * * *